United States Patent
Zhu et al.

(10) Patent No.: US 12,030,921 B2
(45) Date of Patent: *Jul. 9, 2024

(54) FGF ANALOG

(71) Applicant: Jiangnan University, Wuxi (CN)

(72) Inventors: Shenglong Zhu, Wuxi (CN); Yongquan Chen, Wuxi (CN); Zhen Wang, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/819,766

(22) Filed: Aug. 15, 2022

(65) Prior Publication Data

US 2023/0024219 A1 Jan. 26, 2023

Related U.S. Application Data

(63) Continuation of application No. PCT/CN2021/128690, filed on Nov. 4, 2021.

(30) Foreign Application Priority Data

Mar. 12, 2021 (CN) .......................... 202110269910.X

(51) Int. Cl.
| | |
|---|---|
| *C07K 14/50* | (2006.01) |
| *A61K 9/00* | (2006.01) |
| *A61K 38/18* | (2006.01) |
| *A61P 1/16* | (2006.01) |
| *A61P 3/00* | (2006.01) |
| *A61P 35/00* | (2006.01) |

(52) U.S. Cl.
CPC ............ *C07K 14/50* (2013.01); *A61K 9/0019* (2013.01); *A61K 9/0053* (2013.01); *A61K 38/1825* (2013.01); *A61P 1/16* (2018.01); *A61P 3/00* (2018.01); *A61P 35/00* (2018.01)

(58) Field of Classification Search
None
See application file for complete search history.

(56) References Cited

U.S. PATENT DOCUMENTS

| | | | |
|---|---|---|---|
| 8,951,966 B2 * | 2/2015 | Ling .......................... | A61P 3/08 435/243 |
| 2017/0096462 A1 * | 4/2017 | Mohammadi .......... | C07K 14/50 |

FOREIGN PATENT DOCUMENTS

| | | |
|---|---|---|
| CN | 105828833 A | 8/2016 |
| CN | 107108711 A | 8/2017 |
| CN | 108888757 A | 11/2018 |
| CN | 110997726 A | 4/2020 |
| CN | 112851791 A | 5/2021 |
| WO | 2016073855 A1 | 5/2016 |

* cited by examiner

*Primary Examiner* — Christine J Saoud
(74) *Attorney, Agent, or Firm* — IPRO, PLLC

(57) ABSTRACT

The disclosure discloses an anti-metabolic disorder FGF analog and an application thereof, and belongs to the technical field of medicines. According to the disclosure, modification is performed based on an FGF19 mutant NGM282 to obtain a FGF19 analog, and the FGF19 analog is used in treating liver impairment, metabolic disorders, obesity, overweight, metabolic syndrome, diabetes and dyslipidemia and has no side effects of elevated cholesterol and dietary decline in a therapeutic process.

2 Claims, 9 Drawing Sheets

Specification includes a Sequence Listing.

FGF ANALOG

REFERENCE TO SEQUENCE LISTING

The instant application contains a Sequence Listing in XML format as a file named "YGHY-2022-17 SEQ.xml", created on Aug. 12, 2022, of 10928 bytes in size, and which is hereby incorporated by reference in its entirety.

TECHNICAL FIELD

The disclosure relates to a FGF analog and an application thereof, and belongs to the technical field of medicines.

BACKGROUND

Fibroblast growth factor 19 (FGF19), a metabolic regulation factor, is secreted by intestinal cells in response to bile acid to enter intestinal tract to stimulate intestinal secretion and expression. FGF19 secreted by intestinal tract can enter the liver along with cycle and is combined with an FGFR4 in the liver to function. FGF19 has a hormone-like effect, and plays an important role in regulating metabolism, such as in regulating metabolism of bile acid, regulating fullness of gall bladder, improving energy metabolism to reduce body mass, improving blood glucose and the like. Multiple research in early stage indicate that FGF19 plays a role of promoting mitosis, and FGFR4 can promote increase of the FGF19 in the liver and has a tumor-promoting action. In 2014, there have been research finding that the N-terminal domain of FGF19 is a crucial domain interacted with an FGFR. Therefore, selectively knockout of the domain that recognizes an FGFR4 receptor can eliminate the activity of FGF19 promoting mitosis. Thus, several articles have focused on mutation at the N-terminal of FGF19.

An NGM282 is a non-oncogenic engineered variant of human FGF19, which is a mutant modified at the N-terminal of FGF19. Second phase clinical research on the NGM282 has just been completed in US, and the result showed that 79% of patients reached the major treatment endpoint and 34% of patients reached normal liver fat content in the 12th week. The mutant improves liver function and lipid metabolism of the patient and sera biomarkers of fibrosis and shows a curative effect in treating metabolic diseases.

SUMMARY

In view of this, according to the disclosure, modification is performed based on an original non-oncogenic sequence to construct 4 mutant proteins through prediction and test. 4 FGF19 mutant proteins with biological activities are prepared by optimizing production and purification processes. The result shows that the 4 mutants all can play roles of treating obesity, overweight, metabolic syndrome, diabetes, hyperglycemia, dyslipidemia, non-alcoholic steatohepatitis (NASH), atherosclerosis, liver impairment, liver cirrhosis, liver cancer, primary biliary cholangitis (PBC) and primary sclerosing cholangitis (PSC), and the 4 mutants are significantly superior to the NGM282 protein in therapeutic effect.

The disclosure provides an FGF19 protein analog, where an amino acid sequence of the FGF19 protein analog is as shown in any one of SEQ ID NO. 1-4.

In an embodiment, a gene encoding the FGF19 protein analog is provided.

In an embodiment, nucleotide sequences of the encoding gene corresponding to the amino acids shown in SEQ ID NO. 1-4 are as shown in SEQ ID NO. 5-8, respectively.

The disclosure provides a carrier and/or a host cell carrying the gene.

The disclosure provides a drug or a pharmaceutical composition for treating diabetes or obesity, containing the FGF19 protein analog.

In an embodiment, the drug or the pharmaceutical composition further includes a pharmaceutically acceptable carrier agent or excipient.

In an embodiment, the treating diabetes or obesity includes inhibiting body weight gain, reducing blood lipid and blood glucose and improving insulin sensitivity.

The disclosure provides a drug or a pharmaceutical composition for treating hepatitis or related diseases, containing the FGF19 protein analog.

In an embodiment, the drug or the pharmaceutical composition further includes a pharmaceutically acceptable carrier agent or excipient.

In an embodiment, the treating hepatitis or related diseases includes reducing a weight of the liver and a content of triglyceride of the liver, repairing liver impairment, inhibiting expression of an inflammatory cytokine and ameliorating non-alcoholic steatohepatitis, atherosclerosis, liver impairment, liver cirrhosis and liver cancer, primary biliary cholangitis and/or primary sclerosing cholangitis.

The disclosure provides an application of the FGF19 protein analog in preparing a drug for treating one or more of diseases of diabetes, obesity, hepatitis or hepatitis related diseases.

In an embodiment, the drug or the pharmaceutical composition further includes a pharmaceutically acceptable carrier agent or excipient.

In an embodiment, a dosage of the FGF19 protein analog is 0.2-100 mg/kg.

In an embodiment, a dosage of the FGF19 protein analog is 0.2-3 mg/kg.

In an embodiment, an administration route of the drug includes intracutaneous injection, subcutaneous injection, intravenous injection, intramuscular injection, intraperitoneal injection, intravenous drip, arterial injection, intracelial injection and/or oral administration.

The disclosure provides an application of the gene encoding the FGF19 protein analog in preparing a drug for treating diabetes, obesity, hepatitis or hepatitis related diseases.

In an embodiment, nucleotide sequences of the gene are as shown in SEQ ID NO. 5-8, respectively.

The disclosure has the following beneficial effects:

(1) Compared with an original FGF19 mutant NGM282, the 4 new FGF19 analogs provided by the disclosure have more long-acting, more stable and better functions in treating obesity, overweight, metabolic syndrome, diabetes, hyperglycemia, dyslipidemia, non-alcoholic steatohepatitis (NASH), atherosclerosis, liver impairment, liver cirrhosis, liver cancer, primary biliary cholangitis (PBC) and primary sclerosing cholangitis (PSC).

(2) The 4 new FGF19 analogs provided by the disclosure have no side effects of elevated cholesterol and dietary decline caused by the original FGF19 mutant NGM282 in a therapeutic process.

DETAILED DESCRIPTION

Figure 1:
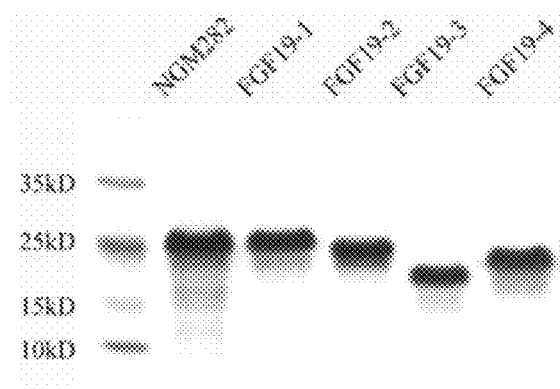
FIG. 1 is an SDS-PAGE electrophoretic analysis chart of expression quantities of purified proteins in *Escherichia coli*, the proteins being FGF19-1, FGF19-2, FGF19-3, FGF19-4 and NGM282 proteins, respectively.

NASH refers to nonalcoholic steatohepatitis.

Experimental animals and feeding: nude mice and db/db mice were purchased from Shanghai SLAC Laboratory Animal Co. Ltd. The mice were raised in the animal center, Wuxi Medical College, Jiangnan University, and lighted alternatively every 12 h at 20+/−2° C.

Cell culture: a hepatoma cell line HepG2 was provided by Institute of Biochemistry and Cell Biology, Chinese Academy of Sciences; DMEM and 0.05% Trypsin were purchased from BOSTER Biological Technology Co., Ltd.; and fetal calf serum was purchased from Sijiqing Co., Ltd.

Other drugs were domestic analytically pure.

The hepatoma cell line HepG2 grew adhering to the wall in a DMEM culture solution containing 10% fetal calf serum, was cultured in a 5% $CO_2$ wet incubator at 37° C., and was passaged every other day.

In the example below, 2 mg/kg FGF21 protein was injected to a mouse, and a corresponding human dosage was 0.2 mg/kg; and 30 mg/kg FGF21 protein was injected to a rabbit, and a corresponding human dosage was 3 mg/kg.

Example 1: Construction, Expression and Purification of a Recombinant Protein (1) Construction of FGF19-1, FGF19-2, FGF19-3 and FGF19-4 Expression Vectors.

4 new FGF19 genes: FGF19-1 (the nucleotide sequence was as shown in SEQ ID NO. 5), FGF19-2 (the nucleotide sequence was as shown in SEQ ID NO. 6), FGF19-3 (the nucleotide sequence was as shown in SEQ ID NO. 7) and FGF19-4 (the nucleotide sequence was as shown in SEQ ID NO. 8) were designed according to computer simulative replacement and preference of an Eco codon. The 4 genes were delivered to Shanghai Generay Biotech Co. Ltd for synthesis, and meanwhile, NdeI and BamHI enzyme cutting sites were designed at two ends of each gene, respectively. The 4 synthesized vectors containing target gene fragments and pET30a (+) were subjected to double enzyme cutting of NdeI and BamHI, and after enzyme cutting was completed, gel extraction was performed to obtain required target fragments. The 4 target fragments were connected with the prokaryotic expression vector pET30a (+) using a T4DNA ligase with a connecting reaction system being 10 μL, the mixture was evenly mixed and connected at 4° C. overnight, and then the four target fragments were converted into Eco DH5a, respectively. Positive clones were selected and were subjected to enzyme cutting identification to construct 4 recombinant plasmids pET30a-FGF19-1, pET30a-FGF19-2, pET30a-FGF19-3 and pET30a-FGF19-4, respectively.

(2) Expression and Purification of Proteins.

The correctly sequenced recombinant plasmids pET30a-FGF19-1, pET30a-FGF19-2, pET30a-FGF19-3 and pET30a-FGF19-4 were converted into competent cells an expression strain Rosseta (DE3). The converted single colony was respectively inoculated to 20 mL of a Kan (50 μg/mL)-containing LB culture medium and cultured for 8 h at 37° C., and then a bacteria solution was inoculated to another 20 ml of a Kan (50 μg/mL)-containing fresh LB culture medium at a volume ratio of 1:100 and cultured at 37° C. When A600 was about 0.35, IPTG was added till a final concentration was 0.25 mmol/L for induction, with an induction temperature being 30° C., thalli were taken out after induction for 5 h, resuspended with Lysis buffer (20 mmol/L Tris, 150 mmol/L NaCl, pH 8.0), crushed, and centrifugalized, and a supernate and a precipitate were taken respectively for 12 wt % SDS-PAGE electrophoretic analysis. Results showed that the expression quantities of the FGF19-1, FGF19-2, FGF19-3 and FGF19-4 proteins were increased significantly, and most target proteins existed in form of inclusion body.

A lot of induced thalli were collected, a lysozyme (1 mg/ml) was added into the thalli, the thalli were placed on ice for 30 min, and cells of the thalli were subjected to ultrasonic cell disruption (working 1 s with an interval of 1 s, 4 min/time, totally 3 cycles). After the thalli were disrupted thoroughly, a cell disruption solution was treated by a QuixStand™ pre-treating system (750 kD ultrafiltration hollow fiber column), the inclusion bodies were enriched, and a liquid at a membrane permeable end was abandoned. When the total volume was about 60 mL, 100 mL of washbuffer (20 mmol/L Tris, 2 mol/L Urea, 150 mmol/L NaCl, pH 8.0) was added to wash the inclusion bodies. When the volume of the solution was 50 mL, 100 ml of a cleaning solution was added into the solution, and the above-mentioned experiments were repeated for 4 times. After washing, when the volume of the solution was 50 mL, the permeable end was closed, and 150 ml of a denaturation solution (20 mmol/L Tris, 10 mol/L Urea, 150 mmol/L NaCl, pH8.0) was added into the washed inclusion bodies for cyclic denaturation for 2 h. The permeable end was opened, and a collected liquid at the membrane permeable end was an mFGF21 denaturation solution. The denaturated mFGF21 was concentrated with a 5KD hollow fiber column and was subjected to renaturation when the volume was 80 mL, and a container filled with a renaturation solution (20 mmol/L Tris, 50 mmol/L NaC, pH 8.0) was connected with a liquid accumulator of the hollow fiber column with a rubber tube. After the liquid accumulator was sealed and the liquid flowed from the permeable end, a negative pressure was generated in the liquid accumulator, so that the renaturation solution was dropwise added into the denaturation solution at a certain rate. When the volume of the added renaturation solution was 6 times of that of the denaturation solution, renaturation was completed, and the solution was centrifugalized for 20 min at 8000 rpm/min at 4° C. to collect a supernate. The renaturation supernate was washed with IEX buffer A 3-4 times of column volume after being fully combined with a Capto Q column (installed in an XK16/20 empty column, the column height being 10 cm and the flow rate being 300 cm/h) balanced by an IEX buffer A (20 mmol/L Tris, 10 mmol/L NaCl, pH 8.0) 5 times of column volume through an AKTApurifier100 system.

When an ultraviolet curve reached a stable baseline, the renaturation supernate was eluted with a mixed solution of the IEX buffer A and the IEX buffer B (20 mmol/L Tris, 1 mmol/L NaCl, pH 8.0), impure proteins were washed with 15 wt % and 100 wt % IEX buffer B solutions, the target proteins were eluted with 18.5 wt %-19 wt % IEX buffer B solutions, eluting peaks were collected, and 15 wt % SDS PAGE electrophoretic analysis was performed. Results showed that the purities of the purified proteins were over 95%. As shown in FIG. 1, a lane 1 is a standard molecular weight Marker of the protein, and lanes 2-6 were purified FGF19-1, FGF19-2, FGF19-3 and FGF19-4, respectively.

Example 2: Detection of In Vivo Half-Life Periods of Recombinant Proteins

In vivo half-life period detection was performed on 5 proteins NGM282, FGF19-1, FGF19-2, FGF19-3 and FGF19-4.

25 rabbits with body weight about 2 kg were selected and divided into 5 groups randomly. 5 proteins NGM282, FGF19-1, FGF19-2, FGF19-3 and FGF19-4 were injected subcutaneously for each group, respectively, with a dosage of 30 mg/kg, and about 800 μl of blood was collected venously at ear veins at 0 h, 1 h, 3 h, 5 h, 7 h and 24 h after administration. Centrifugalization was performed at 12000 r/min for 10 min, and a supernate was taken and stored at 20° C. below zero for later use. The in vivo half-life periods of the 5 proteins were measured by an ELISA indirect method: standard curves of concentration contents of the proteins were respectively established with diluted NGM282, FGF19-1, FGF19-2, FGF19-3 and FGF19-4 proteins with different concentrations (20 μg/mL, 2 μg/mL, 200 ng/mL, 20 ng/ml and 2 ng/ml), the diluted standard proteins and sera were used for coating ELISA plates, the contents of the target proteins in the sera were measured by applying the ELISA indirect method, and the in vivo half-life periods of the 6 proteins were analyzed and calculated statistically.

The in vivo half-life period $t_{1/2}=0.301*(t2-t1)/\log(OD1/OD2)$, where OD1 and OD2 respectively presented average absorbance values on the ELISA plates corresponding to the sera taken out at t1 and t2.

Figure 2:
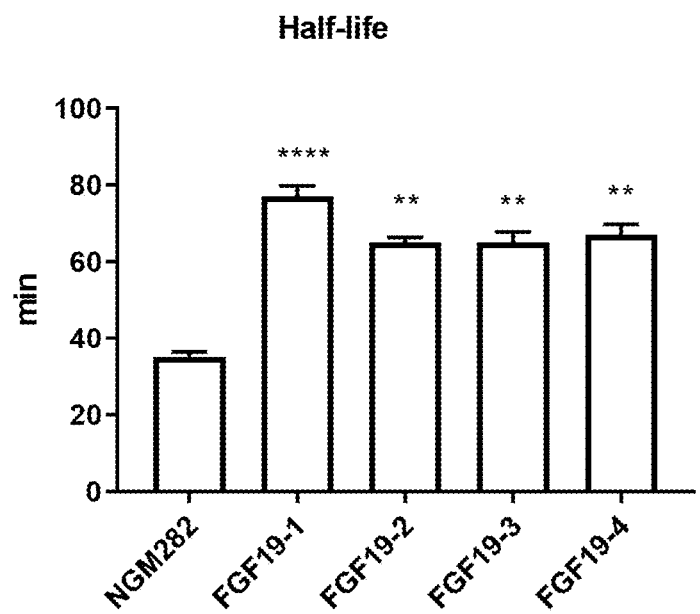
FIG. 2 is a comparison chart of in vivo half-life periods of 5 proteins.

The result was as shown in FIG. 2. The in vivo half-life periods of the NGM282 protein and the proteins FGF19-1, FGF19-2, FGF19-3 and FGF19-4 after mutational modification calculated through a formula were about 36 min, 79 min, 66 min, 67 min and 69 min respectively, indicating that the in vivo half-life periods of the 4 new FGF19-1, FGF19-2, FGF19-3 and FGF19-4 increased significantly.

Example 3: Influence of Recombinant Proteins on Body Weight, Diet, Blood Lipid and Diabetes Related Indexes 4 proteins FGF19-1, FGF19-2, FGF19-3 and FGF19-4 were prepared according to the method in example 1.

50 SPF level 8-weeks old male db/db mice were taken, weighed after being raised for 1 week, and subjected to fasting rather than water deprivation for 6 h next day. Blood of the mice was taken from veins at the tails to measure fasting blood glucose of the mice, mice with abnormal body weights were eliminated. 42 modeled mice with blood glucose and body weight values relatively close to mean values were screened, and were divided into a saline injection group (Saline), a NGM282 group, a FGF19-1 group, a FGF19-2 group, a FGF19-3 group and a FGF19-4 group randomly, with each group containing 6 mice. The mice were given test substances corresponding to the experimental groups once per day at about half past eight every morning by intraperitoneal injection with a dosage of 2 mg/kg, and the saline group was injected with saline same in volume for 8 weeks. In the experimental process, the mice ate and drank freely. During the period, diet and body weight conditions of the mice were monitored.

At 8 weeks after administration, the mice in each experimental group were put to death (fasting at eve), and blood was taken from eyeballs to measure blood glucose, triglyceride (TG), total cholesterol (TC), low density lipoprotein (LDL-C) and high density lipoprotein (HDL-C) levels of the mice. Obtained experimental data was subjected to statistical analysis.

Figure 3:
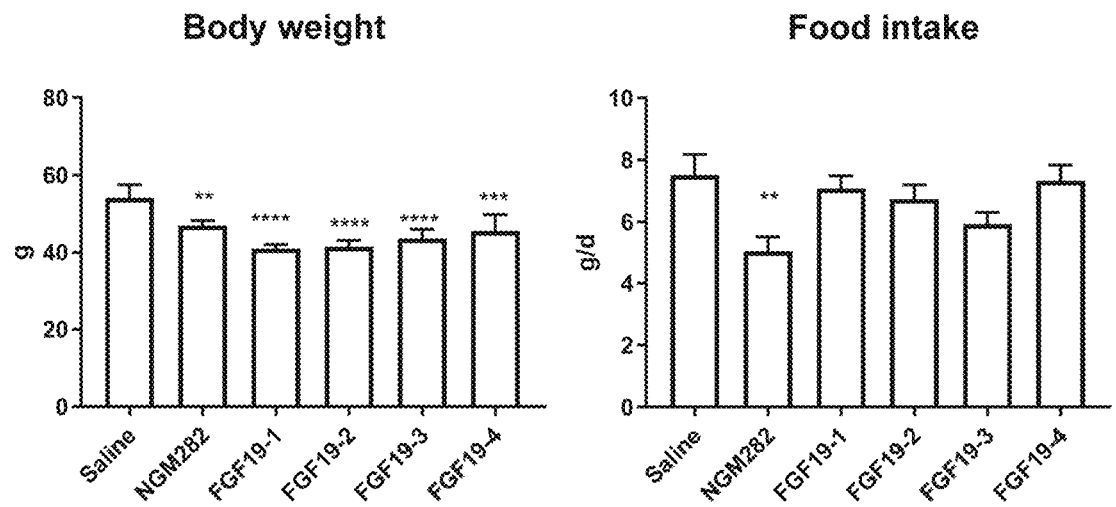
FIG. 3 is an influence diagram of 5 proteins on body weight and diet of a db/db mouse.
Figure 4:
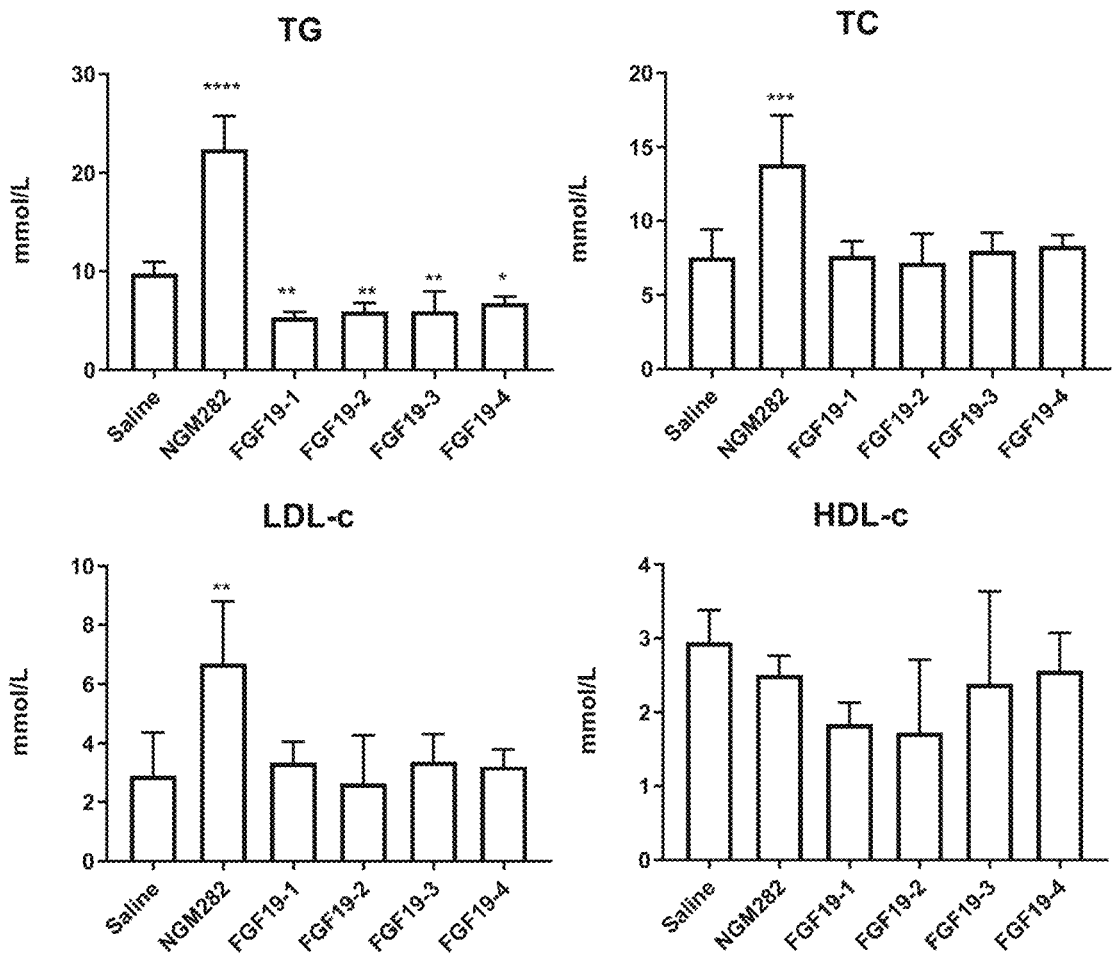
FIG. 4 is an influence diagram of 5 proteins on blood lipid of a db/db mouse.
Figure 5A:
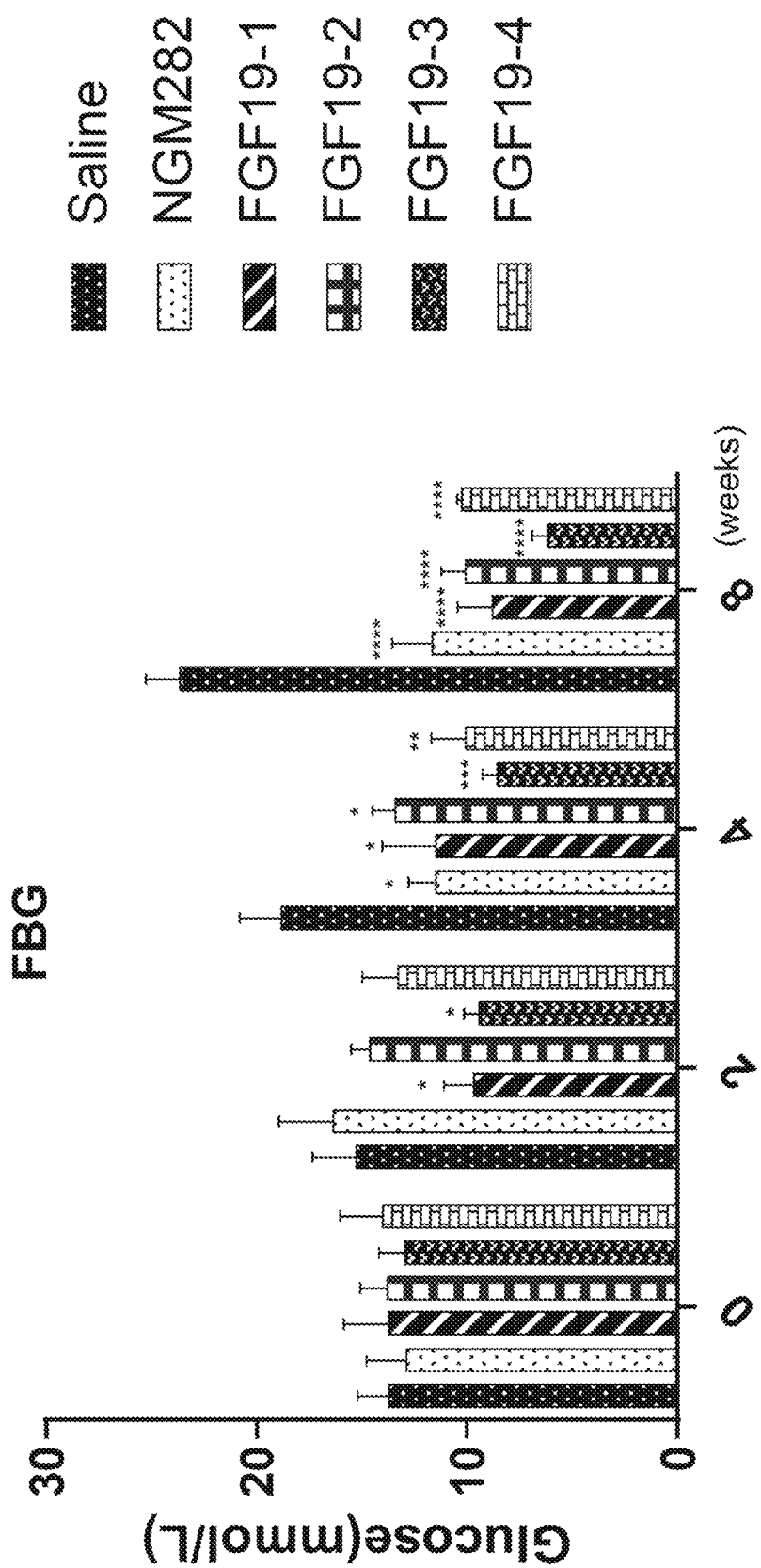
FIG. 5A is an influence diagram of 5 proteins on one of related indexes of diabetes: fasting blood glucose of a db/db mouse.

Experimental detection data was as shown in FIG. 3 to FIG. 5. The result of FIG. 3 indicated that compared with a saline control group, the NGM282 protein and the 4 new proteins FGF19-1, FGF19-2, FGF19-3 and FGF19-4 after mutational modification could reduce body weights of the mice significantly, but the NGM282 protein injection could reduce the volume diet of the mice significantly and inhibit their appetites; while compared with the NGM282, the 4 new proteins FGF19-1, FGF19-2, FGF19-3 and FGF19-4 administrated not only could inhibit the body weights more powerfully and significantly, but also do not affect food intake of the mice, indicating that the mutational modification remedying the side effect of diet decline caused by the original FGF19 successfully.

At 8 weeks after administration, results of blood lipid levels of sera of the mice in the experimental groups were as shown in FIG. 4. Compared with the saline group, the contents of TG, TC and LDL-c in sera of the mice in the NGM282 group were increased significantly, while the contents of various HDL-c had no significant differences, which was consistent with those in many previous clinical reports. Multiple research indicated that elevated cholesterol and blood lipid content is one of prominent high risk factors for metabolic diseases, which was a huge risk for treating the metabolic diseases. After modification, the 4 new proteins FGF19-1, FGF19-2, FGF19-3 and FGF19-4 injected not only did not have side effects of the original FGF19 protein which raised TG, TC and LDL-c, but also could reduce the content of TG in serum significantly. These results further indicated that these mutational modifications remedied side effects of the original FGF19 protein which raised blood lipid successfully, thereby improving the safety and effectiveness of clinical application of the FGF19.

Figure 5B:
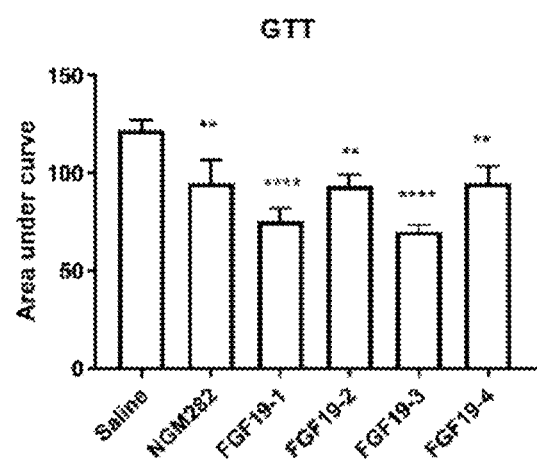
FIG. 5B is an influence diagram of 5 proteins on one of related indexes of diabetes: glucose tolerance of a db/db mouse.
Figure 5C:
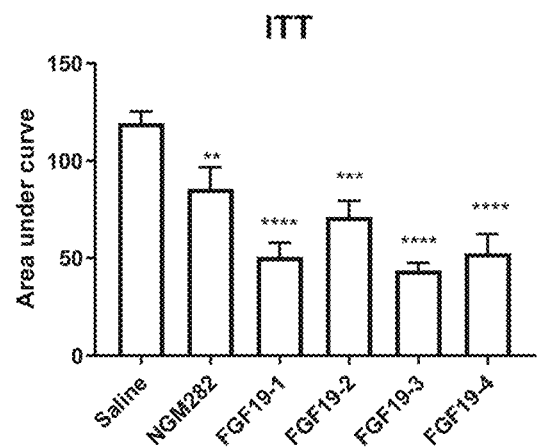
FIG. 5C is an influence diagram of 5 proteins on one of related indexes of diabetes: insulin tolerance of a db/db mouse.

During administration, fasting blood glucose was measured at 0 week, 2 weeks, 4 weeks and 8 weeks respectively. Results of fasting blood glucose levels of the mice in the experimental groups were shown in FIG. 5A. After 2 weeks of treatment, NGM282 has no obvious effect of improving blood glucose, but FGF19-1 and FGF19-3 have reduced fasting blood glucose of the mice significantly. After 4 weeks of treatment, NGM282 started to play a role of reducing blood glucose, but its therapeutic effect was significantly poorer than that of the FGF19-3 and FGF19-4. After 8 weeks, there were no significant differences among the groups. Results indicated that the mutated recombinant FGF19 protein was fast to take effect of reducing blood glucose and was superior to original NGM282. After 8 weeks of administration, a glucose tolerance test and an insulin tolerance test were performed, and results were as shown in FIG. 5B and FIG. 5C. Compared with the NGM282 protein, the 4 new proteins FGF19-1, FGF19-2, FGF19-3 and FGF19-4 after mutational modification could improve glucose sensitivity and insulin sensitivity of the mice with diabetes more significantly.

Example 4: Influence of Recombinant Proteins on Non-Alcoholic Steatohepatitis (NASH)

4 proteins FGF19-1, FGF19-2, FGF19-3 and FGF19-4 were prepared according to the method in example 1.

60 SPF 8-weeks old male C57BL/6 mice were taken and fed with a compound methionine and choline bitartrate deficient (MCD) feed after being raised for 1 week. After being fed for 8 weeks, the mice with abnormal body weights were eliminated. 42 modeled mice with blood glucose and body weight values relatively close to mean values were screened, and were divided into a saline injection group (Saline), a NGM282 group, a FGF19-1 group, a FGF19-2 group, a FGF19-3 group and a FGF19-4 group randomly, with each group containing 6 mice.

The mice were given test substances corresponding to the experimental groups once per day at about half past eight every morning by intraperitoneal injection with a dosage of 2 mg/kg, and the saline group was injected with saline same in volume for 8 weeks. In the experimental process, the mice ate and drank freely. After 8 weeks of administration, the mice in the experimental groups were put to death (fasting at eve); levels of TG, ALP and ALT of livers of the mice were measured, and tissue section staining and inflammatory index detection were performed. Obtained experimental data was subjected to statistical analysis.

Figure 6A:
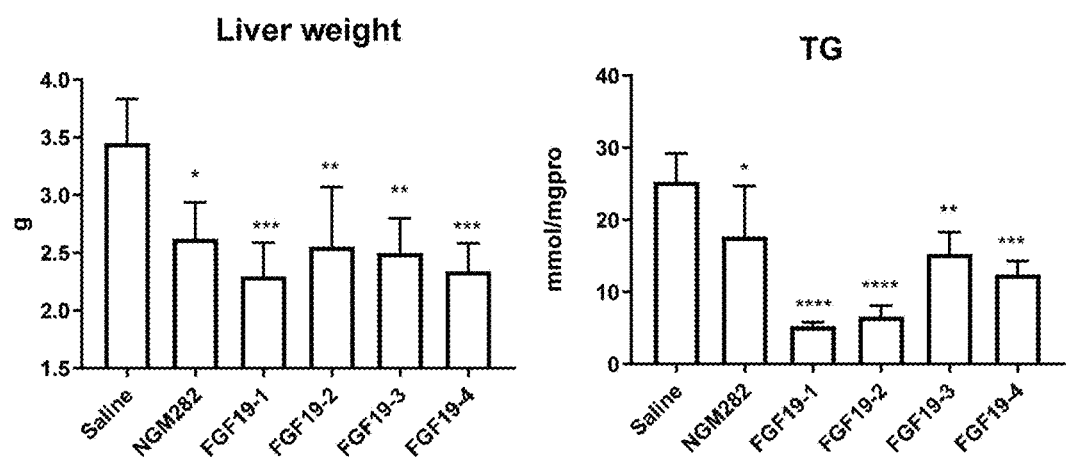
FIG. 6A is an influence diagram of 5 proteins on weight and triglyceride of liver in related indexes such as steatohepatitis and hepatic fibrosis of an NASH model mouse.
Figure 6B:
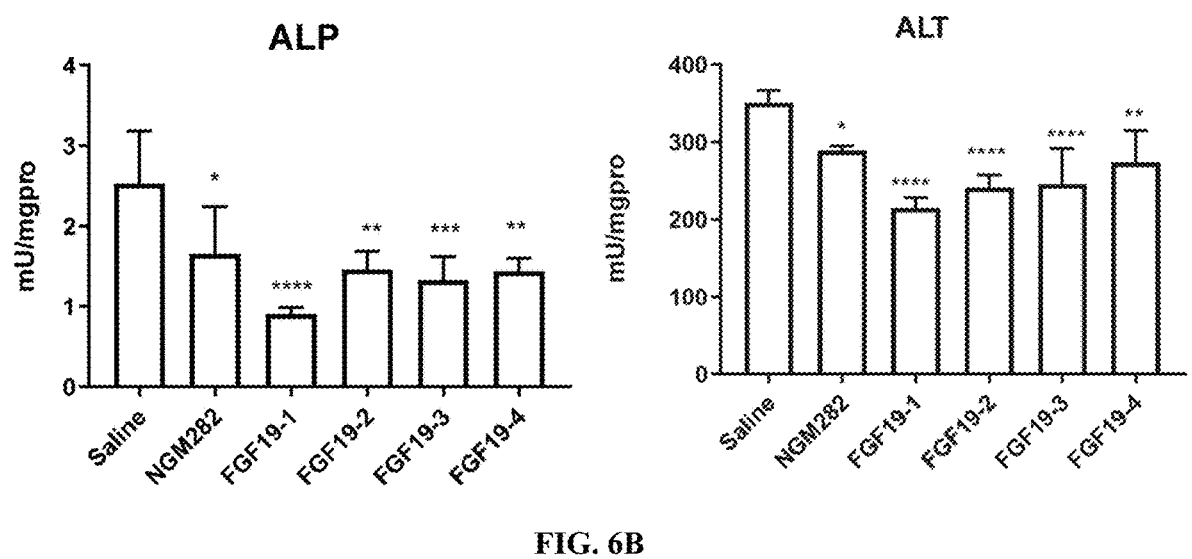
FIG. 6B is an influence diagram of 5 proteins on ALP (alkaline phosphatase) and ALT (alanine aminotransferase) in related indexes such as steatohepatitis and hepatic fibrosis of an NASH model mouse.
Figure 6C:
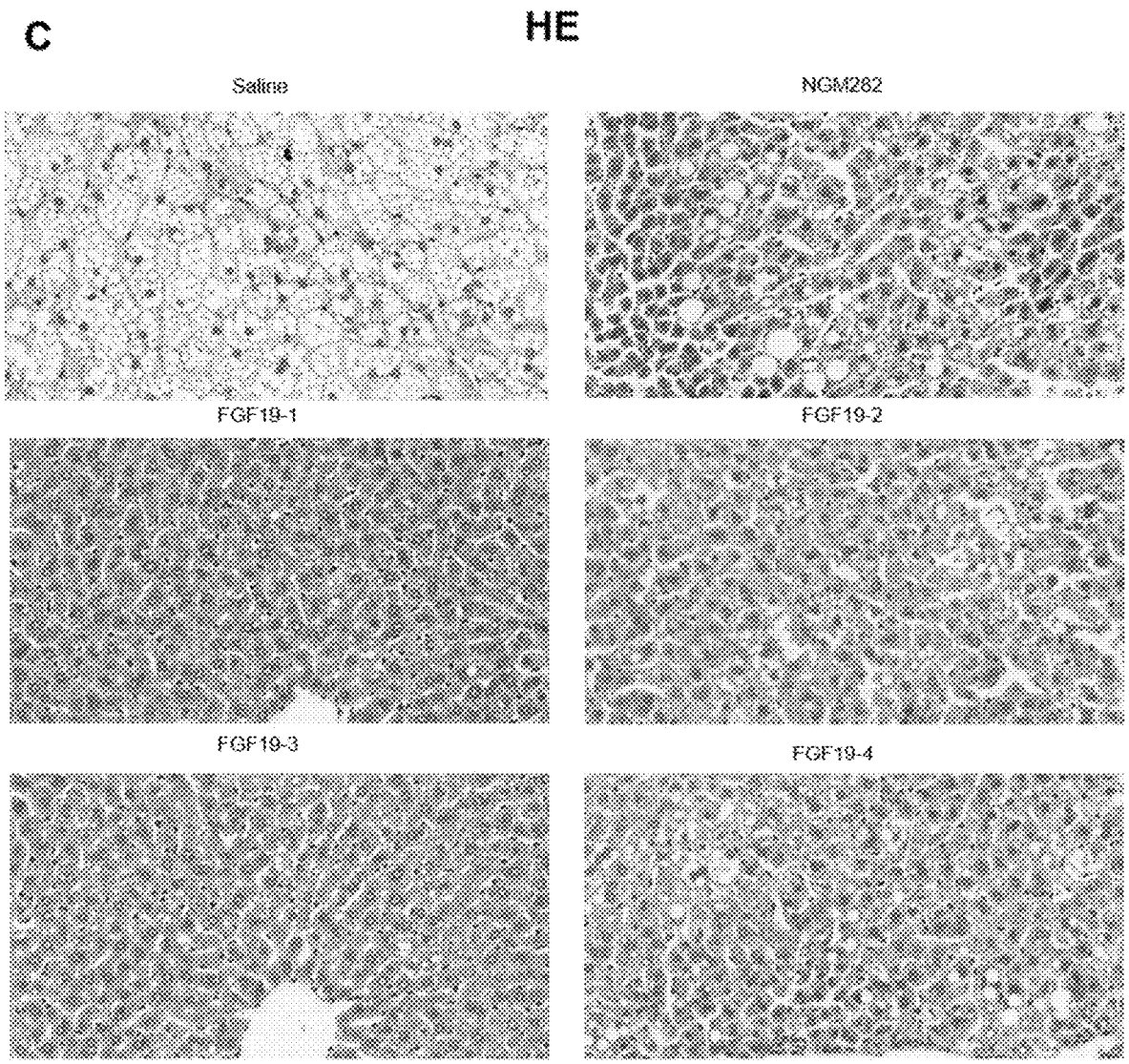
FIG. 6C is an HE staining (hematoxylin-eosin staining) diagram of liver after 5 proteins act on a NASH model mouse.
Figure 6D:
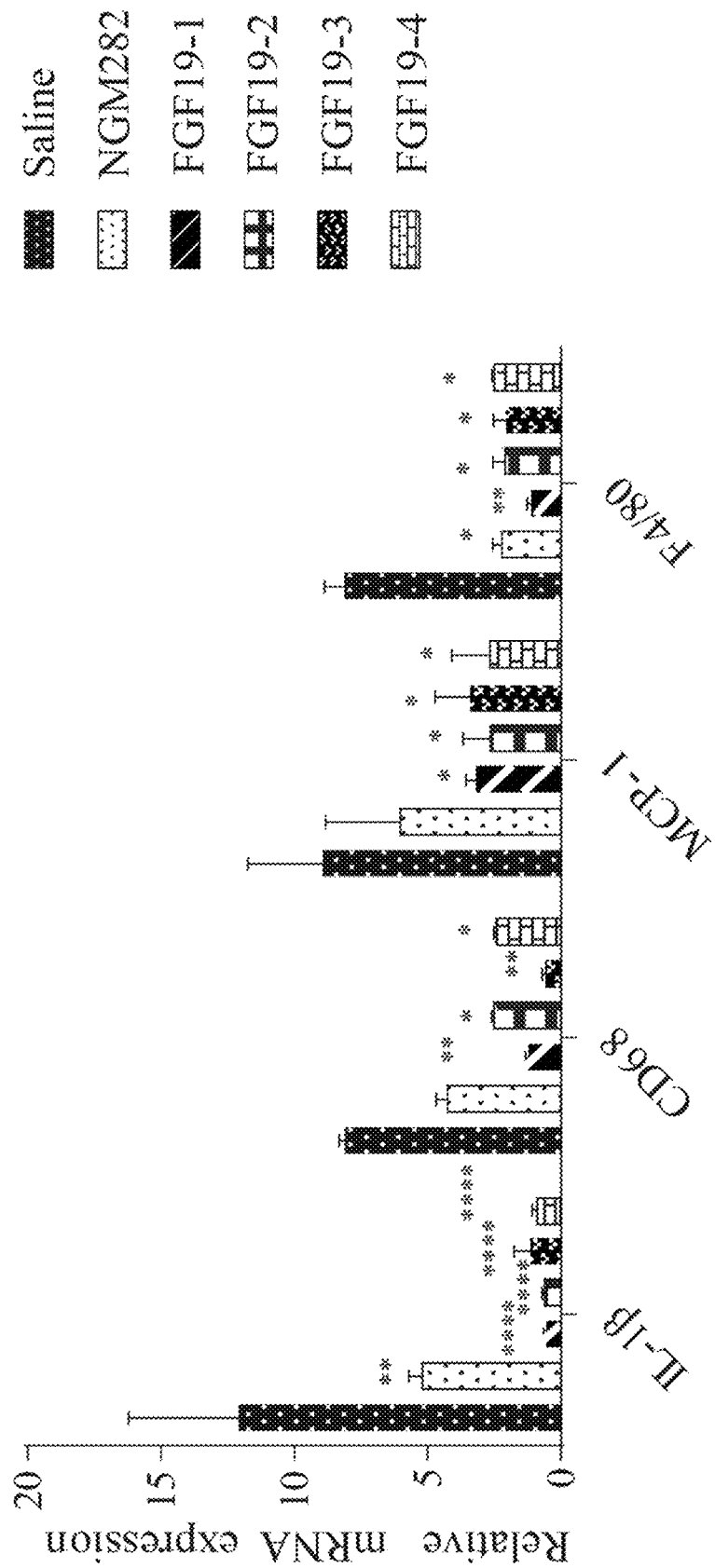
FIG. 6D is the relative expression of the inflammatory cytokine of liver after 5 proteins act on a NASH model mouse.

Experimental detection data was as shown in FIG. 6A-D. Results in FIG. 6A indicated that compared with the saline control group (Saline), the NGM282 protein and the 4 new proteins FGF19-1, FGF19-2, FGF19-3 and FGF19-4 after mutational modification could reduce the weights of the livers of the mice and the contents of TG of the livers significantly, but the 4 new proteins FGF19-1, FGF19-2, FGF19-3 and FGF19-4 were obviously superior to the NGM282 in therapeutic effect. A transaminase result in FIG. 6B further indicated that the 4 new proteins FGF19-1, FGF19-2, FGF19-3 and FGF19-4 were significantly superior to the NGM282 in protecting function to liver impairment. Besides, an HE staining result directly showed that the 4 new proteins FGF19-1, FGF19-2, FGF19-3 and FGF19-4 injected could reduce fat vacuoles of liver significantly; nearly no vacuoles were observed under a microscope, and after treatment by the NGM282, there was still a part of fat vacuoles (FIG. 6C). A picro siuris was red stained for observing deposition of collagenous fibers of livers, reflecting liver fibrosis, and showed that the 4 new proteins FGF19-1, FGF19-2, FGF19-3 and FGF19-4 after mutational modification could reverse liver fibrosis; but after treatment by NGM282, there would be still a part of fibrotic state, indicating that the modified recombinant proteins were superior to the NGM282 in reversal effect on liver fibrosis. A major pathological state of NASH was inflammation in liver. Expression of marker inflammatory cytokines was detected by qPCR. Results showed that the 4 new proteins FGF19-1, FGF19-2, FGF19-3 and FGF19-4 after mutational modification could inhibit expression of the inflammatory cytokines significantly and were superior to the NGM282 in inhibiting effect (FIG. 6D). It was found by detecting multiple index that the 4 new proteins FGF19-1, FGF19-2, FGF19-3 and FGF19-4 after mutational modification were significantly superior to the original NGM282 in therapeutic effect on NASH and liver impairment.

Example 5: Influence of Recombinant Proteins on Liver Cancer 4 proteins FGF19-1, FGF19-2, FGF19-3 and FGF19-4 were prepared according to the method in example 1.

Figure 7:
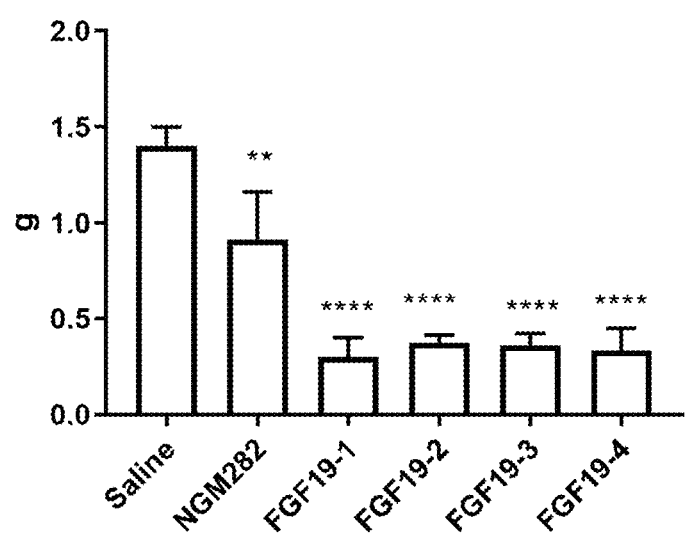
FIG. 7 is an influence diagram of 5 proteins on tumor proliferation of a mouse with hepatic transplantable tumor.

Human hepatoma carcinoma cell HepG2 cells were inoculated subcutaneous to 6-weeks old male nude mice at $1\times10^6$/mouse. The mice were divided into a saline injection group (Saline), a NGM282 group, a FGF19-1 group, a FGF19-2 group, a FGF19-3 group and a FGF19-4 group randomly when tumors grew to 200 $mm^3$, with each group containing 6 mice. The mice were given test substances corresponding to the experimental groups once per day at about half past eight every morning by intraperitoneal injection with a dosage of 2 mg/kg, and the saline group was injected with saline same in volume for 21 days. Volumes of the tumors were monitored every day. The mice were put to death after three weeks, and the weights of the tumors were weighed. Results showed that the 5 proteins all could inhibit both the volumes of transplantation tumors and the final tumor weights, but the NGM282 was significant poorer than the mutated recombinant proteins in inhibiting effect (as shown in FIG. 7).

Although disclosed with preferred embodiments above, the disclosure is not limited by the embodiments. Any of those skilled in the art may make various alternations and modifications without departing the spirit and scope of the disclosure. Therefore, the scope of protection of the disclosure should be subject to the scope of the disclosure as defined in the claims.

What is claimed is:

1. An FGF19 protein analog, wherein the amino acid sequence of the FGF19 protein analog is set forth in SEQ ID NO:4.

2. A drug or a pharmaceutical composition, comprising the FGF19 protein analog according to claim 1 and a pharmaceutically acceptable carrier agent or excipient.

* * * * *

SEQUENCE LISTING

```
Sequence total quantity: 8
SEQ ID NO: 1         moltype = AA  length = 189
FEATURE              Location/Qualifiers
source               1..189
                     mol_type = protein
                     organism = synthetic construct
SEQUENCE: 1
```

```
MRDSSPLVHY GWGDPIRLRH LYTSGPHGLS SCFLRIRADG VVDCARGQSA HSLLEIKAVA    60
LRTVAIKGVH SVRYLCMGAD GKMQGLLQYS EEDCAFEEEI RPDGYNVYRS EKHRLPVCLS   120
SAKQRQLYKN RGFLPLCHFL PMLPMVPEEP EDLRGHLESD MFSSPPDVGS SDPLSMVGPS   180
QGRSPSYAS                                                          189

SEQ ID NO: 2           moltype = AA   length = 178
FEATURE                Location/Qualifiers
source                 1..178
                       mol_type = protein
                       organism = synthetic construct
SEQUENCE: 2
MRDSSPLVHY GWGDPIRLRH LYTSGPHGLS SCFLRIRADG VVDCARGQSA HSLLEIKAVA    60
LRTVAIKGVH SVRYLCMGAD GKMQGLLQYS EEDCAFEEEI RPDGYNVYRS EKHRLPVCLS   120
SAKQRQLYKN RGFLPLPGLP PALPEPPGIL APQPPDVGSS DPLSMVGPSQ GRSPSYAS     178

SEQ ID NO: 3           moltype = AA   length = 191
FEATURE                Location/Qualifiers
source                 1..191
                       mol_type = protein
                       organism = synthetic construct
SEQUENCE: 3
MADSSPLLQF GGQVRQRYLY TDDAQRTEAH LEIREDGTVG GAADQSPESL LQLKALKPGV    60
IQILGVRTPR FLCQRPDGAL YGSLHFDPEA CSFRELLLED GYNVYQSEAH GLPLHLPGNK   120
SPHRDPAPRG PARFLPLCHF LPMLPMVPEE PEDLRGHLES DMFSSPLETD SMDPFGLVTG   180
LEAVRSPSFE K                                                       191

SEQ ID NO: 4           moltype = AA   length = 180
FEATURE                Location/Qualifiers
source                 1..180
                       mol_type = protein
                       organism = synthetic construct
SEQUENCE: 4
MADSSPLLQF GGQVRQRYLY TDDAQRTEAH LEIREDGTVG GAADQSPESL LQLKALKPGV    60
IQILGVRTPR FLCQRPDGAL YGSLHFDPEA CSFRELLLED GYNVYQSEAH GLPLHLPGNK   120
SPHRDPAPRG PARFLPLPGL PPALPEPPGI LAPQPLETDS MDPFGLVTGL EAVRSPSFEK   180

SEQ ID NO: 5           moltype = DNA   length = 567
FEATURE                Location/Qualifiers
source                 1..567
                       mol_type = other DNA
                       organism = synthetic construct
SEQUENCE: 5
atgcgtgata gcagcccgct ggttcattat ggttggggtg atccgattcg tctgcgtcat    60
ctgtatacca gcggtccgca tggtctgagc agctgttttc tgcgtattcg tgcagatggt   120
gttgttgatt gtgcacgtgg tcagagcgca catagcctgc tggaaattaa agcagttgca   180
ctgcgtaccg ttgcaattaa aggtgttcat agcgttcgtt atctgtgtat gggtgcagat   240
ggtaaaatgc agggtctgct gcagtatagc gaagaagatt gtgcatttga agaagaaatt   300
cgtccggatg gttataatgt ttatcgtagc gaaaaacatc gtctgccggt ttgcctgagc   360
agcgcaaaac agcgtcagct gtataaaaat cgtggttttc tgccgctgtg ccattttctg   420
ccgatgctgc cgatggttcc ggaagaaccg gaagatctgc gtggtcatct ggaaagcgat   480
atgtttagca gcccgcccga tgtgggctcc tcggaccctc tgagcatggt gggaccttcc   540
cagggccgaa gccccagcta cgcttcc                                      567

SEQ ID NO: 6           moltype = DNA   length = 537
FEATURE                Location/Qualifiers
source                 1..537
                       mol_type = other DNA
                       organism = synthetic construct
SEQUENCE: 6
atgcgtgata gcagcccgct ggttcattat ggttggggtg atccgattcg tctgcgtcat    60
ctgtatacca gcggtccgca tggtctgagc agctgttttc tgcgtattcg tgcagatggt   120
gttgttgatt gtgcacgtgg tcagagcgca catagcctgc tggaaattaa agcagttgca   180
ctgcgtaccg ttgcaattaa aggtgttcat agcgttcgtt atctgtgtat gggtgcagat   240
ggtaaaatgc agggtctgct gcagtatagc gaagaagatt gtgcatttga agaagaaatt   300
cgtccggatg gttataatgt ttatcgtagc gaaaaacatc gtctgccggt ttgcctgagc   360
agcgcaaaac agcgtcagct gtataaaaat cgtggttttc tgccgctgcc aggcctgccc   420
cccgcactcc cggagccacc cggaatcctg gccccccagc cccccgatgt gggctcctcg   480
gaccctctga gcatggtggg accttcccag gccgaagccc cagctacgc ttcctga      537

SEQ ID NO: 7           moltype = DNA   length = 576
FEATURE                Location/Qualifiers
source                 1..576
                       mol_type = other DNA
                       organism = synthetic construct
SEQUENCE: 7
atggcagact ccagtcctct cctgcaattc gggggccaag tccggcagcg gtacctctac    60
acagatgatg cccagcgtac agaagcccac ctggagatca gggaggatgg acggtgggg   120
ggcgctgctg accagagccc cgaaagtctc ctgcagctga aagcccttaa gccgggagtt   180
attcaaatct gggagtccgt acaccgagg ttcctgtgcc agcggccaga tggggccctg   240
```

```
tatggatcgc tccactttga ccctgaggcc tgcagcttcc gggagctgct tcttgaggac   300
ggatacaatg tttaccagtc cgaagcccac ggcctcccgc tgcacctgcc agggaacaag   360
tccccacacc gggaccctgc accccgagga ccagctcgct tcctgccact atgccatttt   420
ctgccgatgc tgccgatggt tccggaagaa ccggaagatc tgcgtggtca tctggaaagc   480
gatatgttta gcagcccgct ggaaaccgat agcatggacc cgtttggtct ggttaccggt   540
ctggaagcag ttcgtagccc gagctttgaa aaataa                              576

SEQ ID NO: 8           moltype = DNA   length = 543
FEATURE                Location/Qualifiers
source                 1..543
                       mol_type = other DNA
                       organism = synthetic construct
SEQUENCE: 8
atggcagact ccagtcctct cctgcaattc gggggccaag tccggcagcg gtacctctac   60
acagatgatg cccagcgtac agaagcccac ctggagatca gggaggatgg gacggtgggg   120
ggcgctgctg accagagccc cgaaagtctc ctgcagctga agccttgaa gccgggagtt    180
attcaaatct tgggagtccg tacaccgagg ttcctgtgcc agcggccaga tggggccctg   240
tatggatcgc tccactttga ccctgaggcc tgcagcttcc gggagctgct tcttgaggac   300
ggatacaatg tttaccagtc cgaagcccac ggcctcccgc tgcacctgcc agggaacaag   360
tccccacacc gggaccctgc accccgagga ccagctcgct tcctgccact accaggcctg   420
cccccgcac tcccggagcc acccggaatc ctggcccccc agcccctgga aaccgatagc    480
atggacccgt tggtctggt taccggtctg aagcagttc gtagcccgag ctttgaaaaa      540
taa                                                                 543
```